United States Patent [19]

Allen, Jr. et al.

[11] Patent Number: 4,650,817

[45] Date of Patent: * Mar. 17, 1987

[54] PHYSIOLOGICALLY COMPATIBLE ADHESIVE COMPOSITION

[75] Inventors: Douglas Allen, Jr., Bridgewater; Eric Flam, East Brunswick, both of N.J.

[73] Assignee: C. R. Bard, Inc., Murray Hill, N.J.

[*] Notice: The portion of the term of this patent subsequent to Feb. 5, 2002 has been disclaimed.

[21] Appl. No.: 688,964

[22] Filed: Jan. 4, 1985

Related U.S. Application Data

[63] Continuation-in-part of Ser. No. 398,913, Jul. 16, 1982, Pat. No. 4,497,914.

[51] Int. Cl.$^4$ .............................................. C08L 75/00
[52] U.S. Cl. ................................. 523/105; 428/317.1; 428/317.7; 521/109.1; 523/111; 523/121; 524/732; 524/733; 528/49; 604/336; 604/344
[58] Field of Search ...................... 523/105, 111, 121; 524/732, 733; 521/109.1; 528/49; 428/317.1, 317.7; 604/336, 344

[56] References Cited

U.S. PATENT DOCUMENTS

| | | | |
|---|---|---|---|
| 3,302,647 | 2/1967 | Marsan | 128/283 |
| 3,339,546 | 9/1967 | Chen | 523/111 |
| 3,586,648 | 6/1971 | Sambeth et al. | 521/126 |
| 3,980,084 | 9/1976 | Kross | 128/283 |
| 4,011,871 | 3/1977 | Taft | 128/284 |
| 4,160,076 | 7/1979 | Guthrie et al. | 521/159 |
| 4,181,637 | 1/1980 | Busch et al. | 524/733 |
| 4,393,080 | 7/1983 | Pawelchak et al. | 524/17 |
| 4,427,737 | 1/1984 | Cilento et al. | 428/355 |
| 4,496,357 | 1/1985 | Osburn | 604/336 |
| 4,497,914 | 2/1985 | Allen et al. | 523/105 |

Primary Examiner—Maurice J. Welsh
Attorney, Agent, or Firm—Dennison, Meserole, Pollack & Scheiner

[57] ABSTRACT

A new breathable, conformable, polymeric adhesive composition is disclosed which comprises a self-sustaining pressure sensitive adhesive material and a hydrophilic filler, wherein the adhesive material forms a polymeric matrix characterized by the physical encapsulation of the hydrophilic filler within the matrix.

27 Claims, 3 Drawing Figures

PHYSIOLOGICALLY COMPATIBLE ADHESIVE COMPOSITION

This patent application is a continuation-in-part of application Ser. No. 398,913 filed July 16, 1982 now U.S. Pat. No. 4,497,914 issued Feb. 5, 1985.

BACKGROUND OF THE INVENTION

This invention relates to polymeric compositions having the unique ability of providing necessary and desirable properties for skin contact, i.e., breathability, tack, resistance to leakage, dissolution, and disintegration by fluids, and cohesive strength. More particularly, the invention relates to a self-supporting adhesive composition which may be utilized in fabricating a wound dressing, external catheter strip, male exterior catheter, electrode swatch, or a sealing gasket for an ostomy appliance or like medical device. As it is self-supporting, the composition of the invention may be used by itself as a medical device or may be laminated to other materials to fabricate a medical device.

The preparation of medical adhesives which are sufficiently adherent to resist body fluids yet which are sufficiently comfortable has been a difficult proposition. One such adhesive is disclosed in U.S. Pat. No. 3,339,546 and includes a mixture of a viscous gum-like substance and a water-soluble or water-swellable hydrocolloid. The adhesive is applied to a backing and used as a bandage or tape.

A breathable adhesive tape for medical purposes is disclosed in U.S. Pat. No. 4,427,737. This tape includes a porous backing layer and a microporous adhesive comprising a pressure-sensitive rubbery elastomer having dispersed therein a viscous gum-like substance.

Ostomy appliance pads present an especially difficult problem in formulation due to their exposure to body fluids which cause degradation and their need to provide a firm seal to prevent odors. Karaya powder has long been used as an ostomy adhesive, and ostomy appliance pads based upon the inclusion of Karaya powder, such as are disclosed in U.S. Pat. No. 3,302,647, are currently in general use. Karaya has certain disadvantages since it is a nutrient substance and capable of supporting the growth of micro-organisms, not only in use, but when contaminated in storage prior to use. Karaya compositions are lacking in cohesiveness, and therefore tend to disintegrate as well as become slippery when wet often times necessitating the use of a special adhesive to prevent dislocation from the ostomy site.

In U.S. Pat. No. 4,160,076, there is disclosed hydrophilic foams prepared from a capped polyoxyalkylene polyol reactant having a defined average reaction functionality greater than 2, an aqueous reactant and a carefully balanced combination of a nonionic surface-active agent and a liquid defoaming agent. The resultant foams are characterized by a majority of large size cells and membranes which themselves are formed with small cells. In addition, large amounts of many water-soluble or water-dispersable materials such as cellulosic pigments dyes, enzymes or the like may be added to the aqueous reactant. By homogeneously distributing these materials in the aqueous reactant they may be distributed throughout the finally prepared foam. However, the large cell size and membranes characteristic of the hydrophilic polyurethane sponges do not possess the necessary properties of tack, elasticity, sealability and flexibility needed in an ostomy gasket.

An ostomy gasket possessing varying degrees of tackiness, lubricity, and softness is disclosed in U.S. Pat. No. 3,980,084. The polymeric ostomy sealing gasket therein disclosed is formed by the polymerization of a hydroxyalkyl acrylate or methacrylate in the presence of a polyalkylene glycol, reducing agent, or chain terminator, and water. In manufacturing the gaskets, it is essential that the polymerization reaction be carried out in the presence of water. In this manner, a considerable quantity of water is absorbed into the polymer matrix during the polymerization reaction. In addition, natural or synthetic gums or cellulosic type materials to increase absorptive capacity may be incorporated into the polymer matrix. However, the material disclosed has a very low elongation at break and will not return to its original shape after deformation. In addition the materials are often highly viscous and therefore lack the sealability preferred for use in an ostomy device which may result in leakage around the ostomy seal.

Another type of adhesive formulated especially for ostomy care is disclosed in U.S. Pat. No. 4,393,080, and includes a pressure-sensitive adhesive material together with a polymer capable of developing elastomeric properties when hydrated.

OBJECTS OF THE INVENTION

One object of the invention is realized by providing a polymeric composition adapted for use in contact with the skin, derived from curing or solidification of a non-aqueous adhesive liquid precursor having a hydrophilic filler incorporated in the adhesive prior to curing.

Another object of the invention is found in the physical characteristics of the polymeric composition of the present invention, which composition provides a seal with the skin (epidermis) of the human body having a high degree of breathability, tack, elasticity, flexibility, and resistance to leakage, dissolution, and disintegration caused by body fluids. This precludes movement of the seal, and can prevent leakage of fluids around a wound or stomal opening which causes irritation and excoriation if allowed to come into repeated or continuous contact with the skin.

Another object of the invention is to improve the cohesive conformability of the new composition. This property enables the composition to be molded in preferred, self-supporting shapes which inherently adheres to both the patient's skin and an additional structure without the use of additional adhesives. The new composition is soft and resilient, minimizing discomfort when in contact with the skin for extended periods of time.

Still another object of the present invention is to provide medical devices such as tapes and wound dressings which includes an adhesive composition laminated to other supporting layers.

Yet another object of the invention is to extend the shelf life and resistance to contamination of the new composition over Karaya products which have a limited shelf life and harden during storage.

SUMMARY OF THE INVENTION

The polymeric composition of the present invention is prepared by curing or solidification of a non-aqueous liquid precursor resulting in the formation of an adhesive material. Depending on the particular material involved, such solidification may involve a chemical reaction such as a cross-linking reaction, or may involve a physical change such as evaporation of the solvent. A hydrophilic filler, such as a cellulosic or natural gum, is incorporated into the non-aqueous liquid prior to solidification.

A particularly preferred composition is prepared by the reaction of an organic polyisocyanate with one or more di- or greater than di- polyfunctional hydroxyl compounds, for example polyoxyalkylene polyols such as those derived from propylene or ethylene or ethylene oxide, preferably having equivalent weights of at least 500. A monofunctional fatty alcohol may also be incorporated into the reaction mixture in order to provide internal plasticization to increase the accessibility of the fillers to fluids by opening the structure slightly but not so much as to adversely affect the elastomeric properties of the resultant polyurethane matrix composition.

Other adhesive materials which may be used according to the present invention include silicone adhesives, acrylic adhesives, polyvinyl ether adhesives, and adhesives based on styrene copolymers.

The soft polymeric matrix or adhesive composition that is formed by the reaction physically encapsulates the uniformly dispersed hydrophilic filler within the three-dimensional matrix of the resulting self-sustaining adhesive composition. Thus, the product resists dissolution by or passage of bodily fluids while being inherently breathable and hydratable thereby readily allowing migration and transfer of gases such as water vapor. The composition is thus highly suitable both for contact with unbroken skin and with wounds, and is especially suitable for surrounding the stoma as an ostomy pad or gasket. A sealing pad or gasket formed of the composition of this invention is interposed between the face plate of the ostomy device and the skin of the user surrounding the stoma. The sealing pad serves to contain the waste fluids that are highly irritating to the skin and which contain microorganisms of the intestinal tract, and which also give off offensive odors. Additionally, the sealing pad assists in retaining the appliance in place and makes the appliance more comfortable to wear.

Where an occlusive dressing is desired, a composition according to the present invention may be used in conjunction with an impermeable backing material. A pad is then formed from the adhesive laminated to a impermeable backing material, with the adhesive layer being applied to the skin and the impermeable layer away from the skin.

The adhesive composition of the invention may also be formed into a breathable adhesive tape by laminating on one side with a porous polymeric material.

The sealing pad of the invention is especially adapted for performing the foregoing functions. Owing to its compositin, the pad may be cast in any desirable configuration, and it will retain its shape and not break apart in use.

DETAILED DESCRIPTION OF THE INVENTION

Figure 1:
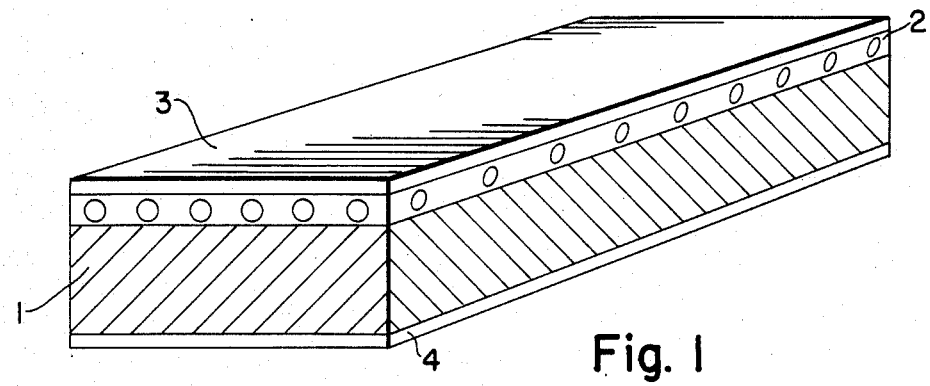
FIG. 1 is a perspective view of an occlusive dressing prepared from a material produced according to the present invention.

One class of compositions according to the present invention is prepared from a polyisocyanate precursor of the general formula $R(NCO)_n$ where n is at least 2, and R is selected from the group consisting of aliphatic, alicyclic, aliphatic-alicyclic, aromatic or aliphatic-aromatic hydrocarbon compounds.

Examples of commercially available polyisocyanates which may be used include liquid isocyanates or polymeric isocyanates based on 4,4'-methyldiphenyl-diisocyanates such as Upjohn Company Isonate 143L, Upjohn Company PAPI 901, Mobay Chemical Corporation Mondur CD, and Mobay Chemical Corporation Mondur MRS-10.

Among the commerically available polyoxyalkylene polyols which may be utilized in the practice of the invention are, for example, Niax Polyol-PPG-3025 (Union Carbide Corporation), Poly-G 55-37 (Olin Chemicals), Poly-G 85-28 (Olin Chemicals), and Multranol 3901 (Mobay Chemical Corporation).

The preferred polyols are Union Carbide Niax Polyol-PPG-3025 and Mobay Multranol 3901, and the preferred monofunctional fatty alcohol is Proctor & Gamble CO-1214. The preferred polyisocyanate is Upjohn Company Isonate 143L.

The proportions and molecular weights of the polyoxyalkylene polyols used, as well as the amounts of the hydrophilic fillers, are governed by the desired characteristics of the final product. Thus, one may tailor products having a diverse range of properties such as tackiness, breathability, cohesiveness and the like.

For example, an elastomer matrix composition formed with diol moieties having nominal equivalent weights of 1500 and triol moieties having nominal equivalent weights of 2000, used in a ratio of approximately 4 to 1 (by equivalents) of diol to triol, yields a particularly desirable product for an ostomy sealing gasket having physically incorporated therein a hydrophilic filler such as hydroxyethylcellulose, hydroxypropyl cellulose or mixtures thereof in the range of approximately 20 to 50% by weight of the final plastic composition.

It has been found that substantially more breathable products are obtained with the use of hydroxyethylcellulose and hydroxypropylcellulose than, for example, with sodium carboxymethylcellulose, karaya gum or polyacrylamide based polyelectrolytes.

In making the breathable elastomeric materials of this invention, the polyol moieties are blended with the hydrophilic filler or fillers to form a homogenous mixture, the consistency of which may vary from a thin cream to a paste. The mixture is then reacted with the polyisocyanate moiety. Techniques such as a one-shot or prepolymer reaction procedure may be employed.

In the prepolymer reaction procedure, the polyol moiety is reacted with an isocyanate to yield longer chains having terminal NCO groups which may later react with additional polyol moieties. This defines in part the physical characteristics of the resulting plastic composition.

For example, the elastomeric matrix product tends to become harder and less conformable as the cross-link density of the structure increases, as for example, with higher functionality polyol and/or NCO moieties. These physical characteristics also are evident if the molecular weight of the polyol moiety is decreased.

The reverse is true, in that as the molecular weight of the polyol moiety is increased, the composition tends to become softer and weaker.

In addition, the stoichiometry affects the final composition as follows. When the NCO/OH ratio is increased, there is a reduction in conformability and tack, while a decrease in the NCO/OH ratio yields a product with increased tack, but decreased strength.

The reaction is catalyzed by known catalysts for such reactions. Suitable catalysts include organic tin esters such as dibutyltindilaurate, tertiary amines, and other catalysts well known in the art.

In addition, a suitable surfactant, such as Dow Corning Antifoam B may be utilized to aid in controlling the uniformity of flow and formation of the resulting plastic compositions.

When the matrix of the present invention is based on a silicone rubber, the starting material is generally a solution of a pressure sensitive adhesive, such as a solution of General Electric PSA6574 in xylene. In order to prepare the gasket, the hydrophilic filler is dispersed in the adhesive solution such as with high speed stirring or with a Cowles dissolver or similar mixer which can produce high shear in solution, or with a Werner-Pfleiderer type mixer, sometimes called a sigma-blade mixer. Thinner mixtures are dispersed better by the high speed Cowles blade, while more viscous mixtures are better handled by the slow speed sigma-blade mixer operating over a period of several hours. When the viscosity of of such a mixture is over 100,000 cps the sigma-blade mixture is clearly preferred, but if it is not available a high speed mixer may be used by adding enough solvent to bring the viscosity down to the range of 80,000 to 100,000 cps. After the paste of adhesive solution and filler is throughly mixed, the solvent is evaporated by spreading the mixture in a layer onto a surface which is non-adherent with respect to the silicone adhesive such as aluminum foil, and drying slowly, preferably for a period of hours at an elevated temperature, but not so hot that bubbles are likely to form. When the solvent is toluene, this temperature is around 60° to 70° C., and for xylene, a temperature of about 100° C. is suitable. The dried film which will be about 1.5 mm in thickness is stripped from the release material and cut into the proper shape for a gasket.

No curing catalyst is used with the silicone adhesive mixture when the resulting gasket is to be used at body temperature. This is highly advantageous since silane curing agents such as gamma-aminopropyltriethoxy silane are apt to irritate the skin and peroxide catalysts must be heated to 150° to 175° C. to be fully effective and at this temperature there may be some discoloration of the hydrophilic fillers. The lack of curing gives a weaker, softer and tackier composition, but the adhesion to skin of the uncured silicones is better than that of the cured silicones.

A gasket formed of the silicone is somewhat weak and stretchy which can be an advantage in fitting it around the stoma. A small hole in the center of the gasket can be enlarged by pushing a wet finger through it, and the enlarged hole will then fit snugly around the stoma. The dimensional stability of the silicone gasket is rather poor, but can be improved by adhering one side of the gasket to the synthetic polymer film used to form the bag of the appliance. If more dimensional stability is desired the composition can be reinforced with synthetic fibers such as cut fibers of polyester, glass or Kevlar. Still more stabilization can be attained by coating 0.5 mm of the silicone composition on each side of a woven fabric such as open weave nylon scrim.

Acrylic polymer adhesives are also available which have good adhesion to human skin and which are not irritating. Such polymer adhesives are available commercially and are made by copolymerizing 2-ethyl hexyl acrylate with a small amount of another acrylate such as methyl or ethyl acrylate or methacrylate and 1 to 5% of a polar acrylic monomer such as acrylic acid. These polymer adhesives are available as solvent solutions and as dispersions in water, an example being the multipolymer solutions sold by Monsanto. In preparing the gasket from the acrylic solution, the hydrophilic filler is added to the acrylic solution much in the same manner as the silicone adhesive solution. The mixture is spread on a release material and preferably allowed to air dry for several hours to remove solvent. The mixture is then heated in an oven at gradually increasing temperatures to remove the remaining toluene, the final temperature being in the range of 110° to 120° C. If the composition which results is excessively soft and stretchy and has poor dimensional stability it can be improved by adding fibers in the manner described with the silicone or the acrylic can be cross-linked with a room temperature cross-linking agent such as triethylene diamine. The catalyst is added shortly before the end of the mixing period. Cross-linking of this type of material increases the shear strength and dimensional stability of the finished gasket, but also reduces the tack and peel strength. The amount of catalyst must be adjusted between the amount which would produce a composition which is sticky but weak, and the amount which would produce a composition which is strong and elastic but deficient in tack and peel strength. The amount of catalyst typically is between 0.03 and 0.2%, based on the weight of the polymer solution. Other curing agents useful for acrylics include polyisocyanates, urea and melamine resins, and methoxymethyl melamine. All of these other cross-linking agents require heat and an acidic catalyst which is less desirable than the room temperature cure with the tertiary amine catalyst.

The compositions of the present invention can also be prepared from styrene copolymers such as Kraton copolymers sold by the Shell Chemical Company. A solution of the styrene copolymer in heptane is generally prepared, and to it is added a tackifier resin and an antioxidant. The hydrophilic filler is than dispersed into the styrene copolymer solution as previously described and the mixture is spread into a layer and the solvent evaporated slowly at 45° C.

The liquid precursor used in the present invention can easily be molded into any desired shape suitable for a skin-contact product, such as catheters, wound dressings, and electrode swatches.

Many suitable adhesive compositions can be obtained by minor variations in the amounts of ingredients employed. The following examples are illustrative of the invention.

EXAMPLE #1

35.0 grams (0.0233 equivalents) of Union Carbide Niax Polyol PPG 3025 (1500 Equivalent Weight polyether diol) and 11.0 grams (0.0055 equivalents) of Mobay Multranol 3901 (2000 EW polyether triol) were blended with 2 drops of M & T Chemical Catalyst T-12 (dibutyltindilaurate) and 1 drop Dow Corning Antifoam B (silicone surfactant). To this mixture, 24.0 grams of Hercules Natrosol 250 HHR hydroxyethylcellulose were blended to form a smooth, homogeneous, creamy liquid.

Then, 4.2 grams (0.0292 equivalents) of Upjohn Isonate 143L (liquid isocyanate based on 4, 4' methyldiphenyldiisocyanate) were added and the mixture thoroughly blended for 60-90 seconds, after which it was poured into an open ⅛" deep sheet mold constructed from silicone release paper. The mixture was allowed to cure until set at room temperature for 1 hour and then cured overnight at 45° C.

The resulting product was a soft, flexible, tacky, self-sustaining elastomer that is light tan in color and possesses high elasticity and conformability. It is breathable and highly durable to body fluids. This combination of properties is ideally suited for use as an ostomy barrier.

EXAMPLE #2

The procedure of Example 1 is repeated, except that the silicone surfactant was deleted. The resulting product was identical to that of Example 1.

EXAMPLE #3

The procedure of Example 1 was repeated using 28.8 grams (0.0192 equivalents) of PPG 3025 and 19.2 grams (0.0096 equivalents) of Multranol 3901.

The resulting product was similar to Example 1, however somewhat lower in tack and elasticity.

EXAMPLE #4

The procedure for Example 1 was repeated using 21.6 grams (0.0144 equivalents) of PPG 3025 and 28.8 grams (0.0144 equivalents) of Multranol 3901.

The resulting product possessed less tack and elasticity than Example 3.

EXAMPLE #5

The procedure for Example 1 was repeated using 43.2 grams (0.0288 equivalents) of PPG 3025 and no Multranol 3901 with 40 drops of catalyst T-12.

The resulting product was highly tacky and soft, exhibiting creep, and not suitable for an ostomy gasket.

EXAMPLE #6

The procedure for Example 1 was repeated using no PPG 3025 and 57.6 grams (0.0288 equivalents) of Multranol 3901.

The resulting product tears easily and has low conformability and tack rendering it unsuitable as an ostomy gasket.

EXAMPLE #7

The procedure for Example 1 was repeated using 36.4 grams (0.0243 equivalents) of PPG 3025 and 9.0 grams (0.0045 equivalents) of Multranol 3901.

The resulting product was very soft and tacky exhibiting a slight tendency to creep.

EXAMPLE #8

The procedure for Example 1 was repeated using 11.7 grams (0.0233 equivalents) of Quaker Oats Polymeg 1000 (500 EW polytetramethylene ether glycol) and 11.0 grams (0.0055 equivalents) of Multranol 3901.

The resulting product had lower conformability, tack, elasticity, and tear strength than Example 1.

EXAMPLE #9

The procedure for Example 1 was repeated using 13.0 grams Hercules Klucel HF hydroxypropylcellulose in place of Natrosol.

The resulting product was whiter than but otherwise similar to Example 1.

EXAMPLE #10

The procedure for Example 1 was repeated using 16.0 grams Natrosol 250 HHR and 8.0 grams Klucel HF.

The resulting product was lighter colored than Example 1 but otherwise similar in properties.

EXAMPLE #11

The procedure for Example 1 was repeated using an initial cure at 45° C. for 15 minutes to set the material followed by overnight cure at room temperature.

The resulting product is similar to Example 1.

EXAMPLE #12

A prepolymer was prepared by mixing 35.0 grams (0.0233 equivalents) of PPG 3025 with 11.0 grams (0.0055 equivalents) of Multranol 3901 and drying the mixture at 100°-110° C. under vacuum at 30 in. Hg.

8.4 grams (0.0584 equivalents) of Isonate 143L were added slowly with thorough mixing and the mixture maintained at 95° C. for 4 hours under nitrogen with frequent mixing. It was then set aside under a nitrogen lid at room temperature until the following day, when a homogeneous mixture of:

35.0 grams (0.0233 equivalents) of PPG 3025,
11.0 grams (0.0055 equivalents) Multranol 3901,
4 drops of T-12 (dibutyltindilaurate),
2 drops antifoam B, and
48.0 grams Natrosol 250 HHR was added. The mixture was thoroughly blended for 60-90 seconds and poured into a sheet mold as in Example 1, cured at room temperature for 1 hour and then at 45° C. overnight.

The resulting product was identical to Example 1.

EXAMPLE #13

A quasi-prepolymer was prepared by mixing 10 grams (0.0694 equivalents) of Isonate 143L into 10 grams (0.0066 equivalents) of PPG 3025 (previously dried at 100°-110° C. under vacuum at 30 in. Hg.). The mixture was maintained under nitrogen at 95° C. for 4 hours with frequent mixing, after which it was set aside under a nitrogen lid at room temperature until the following day.

At that time, 8.4 grams of the quasi-prepolymer were added to a homogeneous mixture consisting of the following:

30.8 grams (0.0205 equivalents) PPG 3025
11.0 grams (0.0055 equivalents) Multranol 3901
4 drops T-12
2 drops Antifoam B
24.0 grams Natrosol 250 HHR The mixture was thoroughly blended for 60-90 seconds and poured into a sheet mold as in Example 1, cured at R.T. for 1 hour, then at 45° C. overnight.

The resulting product was identical to Example 1.

EXAMPLE #14

The procedure for Example 1 is repeated using 35.4 grams (0.0238 equivalents) of PPG 3025 polyether diol, 10 grams (0.0050 equivalents) of Multranol 3901 polyether triol, 0.38 grams (0.0019 equivalents) of Proctor and Gamble CO-1214 monofunctional fatty alcohol and 5.3 grams (0.0368 equivalents) of Isonate 143L.

The resulting product was similar to the product of Example 1.

EXAMPLE #15

The procedure for Example 14 is repeated except that 0.75 grams (0.0038 equivalents) of CO-1214 are used with 5.6 grams (0.0389 equivalents) of Isonate 143L.

The resulting product tears easily and has low conformability.

EXAMPLE #16

Into 100.0 grams of General Electric PSA6574 pressure sensitive silicone adhesive solution (55% solids in toluenenaphtha) are dispersed 16.0 grams of hydroxyethylcellulose to form a homogeneous pasty liquid. After the paste is thoroughly mixed, it is spread into an open ⅛" deep sheet mold and the solvent evaporated by heating slowly at an elevated temperature of approximately 70° C., but not so hot that bubbles form.

The resulting product is similar to that of Example 1.

EXAMPLE #17

Into 100.0 grams of Monsanto Gelva Multipolymer Solution RA-788 pressure sensitive acrylic adhesive (40% solids in ethyl-acetate-toluene mixture) are dispersed 16.0 grams of hyroxyethycellulose to form a homogeneous paste. After the paste is thoroughly mixed, it is spread into an open sheet mold and the solvent evaporated by heating slowly at approximately 70° C.

The resulting product is similar to that of Example 1.

EXAMPLE #18

Into 1000 grams of Monsanto Multipolymer Solution RA-1159 (34% solids) are added 68 grams guar gum and 68 grams hydroxyethylcellulose and the mixture is mixed thoroughly in a dough mixer for about one hour. A mixture of two parts ethyl-acetate and one part isopropanol is added to restore solvent which evaporated during mixing. About five minutes before the end of the mixing period, 1.5 grams of Dabco catalyst comprising triethylene diamine is added as a 10% solution in toluene. The mixture is spread in a mold, and allowed to polymerize at room temperature to produce a product with greater dimensional stability than that of Example 17, but with lower tack.

EXAMPLE #19

A solution is prepared from 20.0 grams of Shell Chemical Company Kraton D1107 styrene copolymer, 0.2 grams of Monsanto Santovar A antioxidant, 8.0 grams of Hercules Hercolyn D tackifier resin and 26.0 grams of Hercules Piccotac B-BHT tackifier resin in 50.0 grams of heptane. Into this solution is dispersed 16.0 grams of hydroxyethylcellulose to form a homogeneous pasty liquid, which after thorough mixing is spread into a sheet mold and the solvent evaporated slowly at 45° C.

The resulting product is similar to that of Example 1.

EXAMPLE #20

A wound dressing as shown in FIG. 1 is prepared from an adhesive produced according to the procedure of Example 1. This product is designated as layer 1 in FIG. 1. A flexible foam layer 2 comprising 35 mil polyethylene is laminated to adhesive sheet 1 and an impermeable backing 3 is coated on or laminated to foam layer 2. The foam layer may also be omitted. A release liner 4 is applied to the skin contacting side of adhesive sheet 1 and the product is cut into squares or other desired shapes.

The resulting product attaches securely to normal skin, such as that surrounding the wound. The composition is hydratable and transforms into a soft, moist, gelatinous surface over the wound. The dressing provides leak proof protection against bacteria and removes gently in one-piece without damaging the newly formed tissue in the wound bed.

EXAMPLE #21

Figure 2:
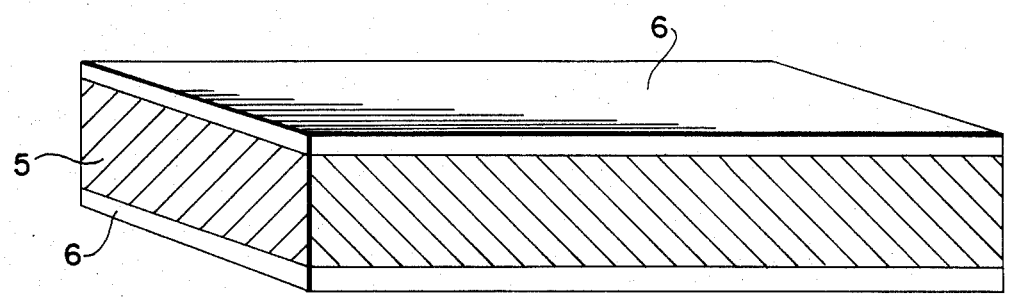
FIG. 2 is a perspective view of a male external catheter strip produced from a material prepared according to the present invention.

A male external catheter strip as shown in FIG. 2 is formed from an adhesive composition as prepared in Example 1. A sheet 5 of the adhesive is covered on both sides with a release liner 6 and is cut into strips convenient for use.

The product provides secure, leak resistant, breathable adhesion between catheter sheath and skin. It possesses high elasticity and conformability for maximum comfort and safety.

EXAMPLE #22

Figure 3:
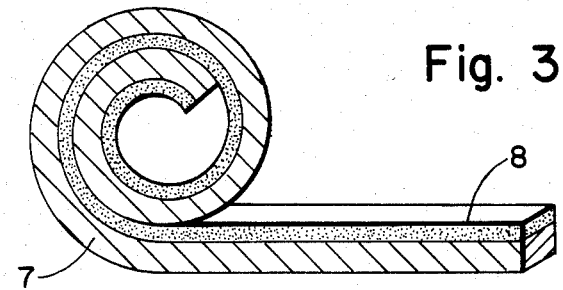
FIG. 3 is a perspective view of a breathable adhesive tape prepared with a material produced according to the present invention.

A breathable adhesive tape as shown in FIG. 3 is formed from a sheet 7 of the adhesive material as prepared in Example 1. The sheet is covered on one side with a porous backing 8 such as an open mesh polyethylene or a polymeric foam such as polyethylene or polyurethane. The tape can be cut and packaged on strips or wound into rolls.

What is claimed is:

1. A polymeric composition, for providing an elastomeric adhesive, breathable, cohesive, conformable, self-supporting body fluid generally non-degradable composition for use as a medical device in adherent contact with the skin, which comprises an adhesive product selected from the group consisting of a polyurethane adhesive, a silicone adhesive, an acrylic adhesive based on a copolymer of 2-ethyl hexyl acrylate, a polyvinylether adhesive, and an adhesive based on styrene copolymers, said adhesive product formed by solidifying a substantially non-aqueous liquid adhesive precursor, said polyurethane adhesive product derived from the generally non-aqueous reaction of an organic polyisocyanate, and a polyoxyalkylene polyol moiety comprising a mixture of a major portion of polyol having a diol functionality and a minor portion of polyol of at least triol functionality, said adhesive product having incorporated a hydrophilic filler wherein there is provided a polymeric matrix characterized by the physical encapsulation of the hydrophilic filler within the polymeric matrix.

2. The composition of claim 1, wherein a monofunctional fatty alcohol is added to said generally non-aqueous reaction.

3. The composition of claim 1 wherein said organic polyisocyanate is of the general formula $$R(NCO)_n$$

where R is selected from the group consisting of aliphatic, alicyclic, aliphatic-alicyclic, and aromatic or aliphatic-aromatic hydrocarbon compounds and n is at least 2, and the polyoxyalkylene polyol moiety is of the general formula $R(OH)_{n'}$ where R is a polyoxyalkylene and n' is at least 2.

4. The composition of claim 1 wherein said polyol moiety consists of diols of nominal equivalent weights of 1500 and triols of nominal equivalent weights of 2000 in a ratio of approximately 4 to 1 of diol to triol.

5. The composition of claim 1 wherein said polyisocyanate is a liquid isocyanate based on 4,4" methyldiphenyldiisocyanate and said polyol moiety is a mixture of 1500 equivalent weight polyether diol and 2000 equivalent weight polyether triol.

6. The composition of claim 1 wherein said hydrophilic filler is selected from the group consisting of hydroxyethylcellulose, hydroxypropylcellulose, and mixtures thereof.

7. The composition of claim 1 wherein said medical device is an ostomy gasket.

8. The composition of claim 1 wherein said medical device is a wound dressing.

9. The composition of claim 8, additionally comprising an impermeable backing layer in contact with the adhesive composition.

10. The composition of claim 9, wherein said impermeable backing layer comprises a polyvinylidene chloride film.

11. The composition of claim 9, additionally comprising a flexible foam layer interposed between said adhesive composition and said impermeable backing layer.

12. The composition of claim 1, wherein said medical device is a male external catheter strip.

13. The composition of claim 1, wherein said medical device is a breathable adhesive tape.

14. The composition of claim 13, wherein said adhesive composition is covered on one side with a porous backing layer.

15. The composition of claim 14, wherein said porous backing layer is selected from the group consisting of an open mesh polyethylene and a polymeric foam.

16. The composition of claim 15, wherein said polymeric foam is a polyethylene or polyurethane foam.

17. The composition of claim 1, wherein said medical device is an electrode swatch.

18. A method for providing an elastomeric adhesive, breathable, cohesive, conformable, self-supporting, body fluid generally non-degradable composition for use as a medical device in adherent contact with the skin, comprising the steps of forming a substantially non-aqueous liquid precursor of a polymeric pressure sensitive adhesive material selected from the group consisting of polyurethane adhesives, silicone adhesives, acrylic adhesives based on copolymers of 2-ethyl hexyl acrylate, polyvinylether adhesives and adhesives based on styrene copolymers, dispersing in said precursor a hydrophilic filler, and solidifying said filled precursor to form a polymeric composition comprising a polymeric matrix having the hydrophilic filler encapsulated therein, said polyurethane precursor being an organic polyisocyanate solidified by a generally non-aqueous reaction with a polyoxyalkylene polyol moiety comprising a mixture of a major portion of a polyol having a diol functionality and a minor portion of a polyol of at least triol functionality.

19. The method of claim 18 wherein said polymeric composition is a reaction product of said precursor.

20. The method of claim 18 wherein said liquid precursor additionally comprises a monofunctional fatty alcohol.

21. The method of claim 18 wherein said organic polyisocyanate is of the general formula $R(NCO)_n$ where R is selected from the group consisting of aliphatic, alicyclic, aliphatic-alicyclic, and aromatic or aliphatic-aromatic hydrocarbon compounds and n is at least 2, and said polyoxyalkylene polyol moiety is of the formula $R(OH)_{n'}$ where R is a polyoxyalkylene and n' is at least 2.

22. The method of claim 18 wherein said liquid precursor comprises a solution of a pressure sensitive adhesive material having a solvent which evaporates during said solidification.

23. The method of claim 22 wherein a curing catalyst is incorporated into said solution.

24. The method of claim 23 wherein said liquid precursor is selected from the group consisting of solutions of silicone adhesives, solutions of acrylic adhesives, and solutions of styrene copolymers.

25. The method of claim 18 wherein said hydrophilic filler is selected from the group consisting of hydroxyethylcellulose, hydropropylcellulose, and mixtures thereof.

26. A method for providing an elastomeric adhesive, breathable, cohesive, conformable, self-supporting, body fluid generally non-degradable composition for use as a medical device in adherent contact with the skin, comprising the steps of forming an aqueous liquid precursor of an acrylic adhesive based on copolymers of 2-ethyl hexyl acrylate, dispersing in said precursor a hydrophilic filler, and solifiying said filled precursor to form a polymeric composition comprising a polymeric matrix having said hydrophilic filler encapsulated therein.

27. A polymeric composition for providing an elastomeric adhesive, breathabel, cohesive, conformable, self-supporting, body fluid generally non-degradable composition for use as a medical device in adherent contact with the skin, which comprises an acrylic adhesive based on a copolymer of 2-ethyl hexyl acrylate, said adhesive derived from an aqueous liquid precursor of said copolymer, said adhesive having incorporated therein a hydrophilic filler wherein there is provided a polymeric adhesive matrix characterized by the physical encapsulation of said hydrophilic filler within said polymeric matrix.

* * * * *